United States Patent
Zhao et al.

(10) Patent No.: US 10,470,879 B2
(45) Date of Patent: Nov. 12, 2019

(54) HEART VALVE BIOPROSTHESIS AND MANUFACTURING METHOD THEREOF

(71) Applicant: HANGZHOU JIAHEZHONGBANG BIOTECHNOLOGY CO., LTD, Hangzhou, Zhejiang (CN)

(72) Inventors: Yimin Zhao, Beijing (CN); Hao Zhang, Hangzhou (CN)

(73) Assignee: HANGZHOU JIAHEZHONGBANG BIOTECHNOLOGY CO., LTD (CN)

( * ) Notice: Subject to any disclaimer, the term of this patent is extended or adjusted under 35 U.S.C. 154(b) by 54 days.

(21) Appl. No.: 15/568,064

(22) PCT Filed: Mar. 2, 2016

(86) PCT No.: PCT/CN2016/075359
§ 371 (c)(1),
(2) Date: Nov. 16, 2017

(87) PCT Pub. No.: WO2016/169338
PCT Pub. Date: Oct. 27, 2016

(65) Prior Publication Data
US 2018/0133002 A1    May 17, 2018

(30) Foreign Application Priority Data

Apr. 20, 2015 (CN) .......................... 2015 1 0189387

(51) Int. Cl.
*A61F 2/24* (2006.01)
*A61L 27/36* (2006.01)

(52) U.S. Cl.
CPC .............. *A61F 2/2415* (2013.01); *A61F 2/24* (2013.01); *A61F 2/2409* (2013.01);
(Continued)

(58) Field of Classification Search
CPC .... A61F 2/2409; A61F 2/2418; A61F 2/2415; A61F 2220/0075; A61F 2230/0013;
(Continued)

(56) References Cited

U.S. PATENT DOCUMENTS 4,470,157 A * 9/1984 Love ...................... A61F 2/2409
                                                                    623/2.15
4,501,030 A * 2/1985 Lane ...................... A61F 2/2418
                                                                    623/2.18
(Continued)

*Primary Examiner* — Paul B Prebilic
(74) *Attorney, Agent, or Firm* — Law Offices of Albert Wai-Kit Chan, PLLC

(57) ABSTRACT

A heart valve bioprosthesis (100) and a manufacturing method thereof are provided. The heart valve bioprosthesis (100) comprises: a support frame (1), valve leaflets (2) and a valve auxiliary structure. The valve leaflets (2) are connected to the valve auxiliary structure, the valve auxiliary structure is connected to the support frame (1). Both the valve leaflets (2) and the valve auxiliary structure are made of biological tissues. The support frame (1) is formed as a single component with an elastic material, and the valve auxiliary structure is preset with suturing marks. The heart valve bioprosthesis improves the biocompatibility with the human body, reduces the total height of the valve, shortens the suturing time, and decreases the possibility of thrombus or bacterial attachment thereto. In addition, the heart valve bioprosthesis is made by a simple process, exhibit excellent compliance with the cardiac tissue, and has a prolonged service life.

13 Claims, 15 Drawing Sheets

(52) U.S. Cl.
CPC .......... *A61F 2/2412* (2013.01); *A61F 2/2418* (2013.01); *A61F 2220/0075* (2013.01); *A61L 27/3625* (2013.01)

(58) Field of Classification Search
CPC ...... A61F 2210/0076; A61F 2230/0065; A61F 2230/0095; A61F 2240/001; A61F 2250/0097; A61F 2250/007
See application file for complete search history.

(56) References Cited

U.S. PATENT DOCUMENTS

| | | | | |
|---|---|---|---|---|
| 4,680,031 | A * | 7/1987 | Alonso | A61F 2/2409 623/2.13 |
| 4,759,758 | A * | 7/1988 | Gabbay | A61F 2/2412 623/2.13 |
| 8,585,757 | B2 * | 11/2013 | Agathos | A61F 2/2418 623/2.17 |
| 2004/0078950 | A1 * | 4/2004 | Schreck | A61F 2/2412 29/447 |
| 2011/0029072 | A1 * | 2/2011 | Gabbay | A61F 2/2409 623/2.23 |
| 2011/0276128 | A1 * | 11/2011 | Cao | A61F 2/2409 623/2.11 |

\* cited by examiner

HEART VALVE BIOPROSTHESIS AND MANUFACTURING METHOD THEREOF

FIELD OF THE INVENTION

The present invention relates to a heart valve bioprosthesis used in a cardiovascular surgery (cardiac surgery).

BACKGROUND OF THE INVENTION

In the medical field of cardiovascular surgery, if any lesion occurs to the valve inside the heart due to some reason(s) to cause hypofunction of the heart, and internal medicine fails, it is generally necessary for surgeons to employ a surgical implantation approach where the affected valve that have lost its original function will be replaced with a valve prosthesis. Such heart valve prosthesis for the implantation surgery is currently classified into two types: the mechanical heart valve prosthesis and the heart valve bioprosthesis. The present invention concerns heart valve bioprosthesis. Depending on whether a stent (support frame) is present inside the valve, the heart valve bioprosthesis is classified into stented valve (support frame) and stentless valve (no support frame).

A stentless valve (no support frame) is made purely of biological tissues or a combination of biological tissues and terylene fabric. The valve leaflet is made of bovine, equine or porcine pericardium. The covering and suture edge (ring) is made of bovine or equine pericardium and/or terylene fabric. The stentless valve has the following advantages: due to the absence of a stent, it has outstanding compliance with the heart after implantation; the various parts of the valve leaflet experience minimal stresses and relatively little damage, thus having a long service life. The stentless valve has the following disadvantages: also due to the absence of stent (no support frame), positioning the valve is quite difficult during an implantation operation, so that the surgeon needs to have a high skill level, and it is difficult for the surgeon to perform precise implantation. Thus, its use is limited.

A stented valve (support frame) is generally made of three materials: metals or plastics, biological tissues, and terylene fabric (also called polyester fiber or polyethylene terephthalate or PET, hereinafter as terylene for short). Currently, the stented bioprosthetic valves (support frame) accounts for 95% of the valve bioprosthesis. The stented valve has the following advantages: due to the presence of a stent (support frame), it is convenient to position during surgical implantation, facilitating precise implantation by the surgeon. However, existing stented valves are traditionally made of three materials: biological tissues for making the valve leaflet, metallic (alloy) or polymeric material for making the support frame, and terylene fabric for making the covering material and the suture edge (ring). Such type of valves has the following disadvantages: 1) the terylene fabric, after implantation into the heart and being exposed to blood, leads to relatively high possibility of thrombus or increased bacterial attachment; 2) the support frame, as a structure formed by combination of metallic wires and a base made of metallic plates, is high in hardness but poor in elasticity and compliance, and the valve leaflets fatigue easily; 3) the support frame, being a structure formed by combination of metallic wires and a metallic base, is structurally complicated and difficult to manufacture, weldings between the metallic wires will potentially break; and 4) the valve has a relatively large total height such that the aortic valve tends to block the blood flow at the opening of the coronary artery and the mitral valve tends to impede the movement of the original sub-valvular structures after implantation into the heart.

Terylene fabric is used for making the covering material and suture ring for both stented and stentless valves. This is because, on the one hand, terylene fabric has excellent chemical inertness, sterilization resistance, good mechanical properties, low water absorption and relatively good biocompatibility. Specifically, terylene fabric can be sterilized by traditional technologies, without changing its inherent properties, and has many advantages, such as high strength, good elasticity, good wear resistance, good fatigue resistance, and good dimensional stability, etc. Also, terylene fabric has relatively good chemical inertness, can induce tissue growth, reacts well to fibrosis, and has been proved safe during its more than 50 years history of implantation. On the other hand, as it has a use history of decades, those skilled in the art, will generally use terylene fabric when designing the covering material and suture ring.

In addition, for manufacturing any type of heart valve prosthesis, different components have to be sutured manually. The suturing points and the spacing between these points depend solely on the experience of the technical operators, and it is difficult to control suturing quality and provide training.

In view of the outmoded design concept of the traditional heart valve bioprosthesis, the present invention is designed and developed to overcome the many disadvantages in use and function as a result of the complicated structure.

SUMMARY OF THE INVENTION

The objective of the present invention is to provide a heart valve bioprosthesis which can decrease thrombus or bacterial attachment. Another objective of the present invention is to solve the technical problems of the complicated valve structure, support frame being too hard, and poor compliance with the heart. Another objective of the present invention is to solve the problem of suturing based solely or mainly by experience during manufacturing of a traditional valve bioprosthesis which prevent the procedures from being standardized.

In order to achieve the above objectives, according to an aspect of the present invention, a heart valve bioprosthesis is provided, said heart valve bioprosthesis comprises: a support frame, a plurality of valve leaflets and a valve auxiliary structure, wherein the plurality of valve leaflets is connected to the valve auxiliary structure, the valve auxiliary structure is connected to the support frame, and the plurality of valve leaflets and the valve auxiliary structure are made of biological tissues.

In an embodiment, the valve auxiliary structure may comprise a suture ring and a covering material, the plurality of valve leaflets is connected to the covering material, and the covering material and the suture ring are fixed directly or indirectly on the support frame.

Preferably, the plurality of valve leaflets is sutured to the covering material. Preferably, the covering material is fixed to the support frame, and the suture ring is connected to the covering material.

Preferably, the support frame comprises a valve ring and a valve ridge which are formed as a single component, and the suture ring is sutured to an outer side edge of the valve ring.

In an embodiment, the covering material may comprise an inner covering and an outer covering, wherein the plurality of valve leaflets is connected to the inner covering, and the support frame is placed within a space formed between the inner covering and the outer covering.

The inner covering and the outer covering are sutured together to form the upper and lower edges of the covering material with the support frame.

Preferably, the plurality of valve leaflets is sutured to the top edge of the inner covering and the top edge of the outer covering is sutured to the top edge of the inner covering to form the upper edge of the covering material; and the lower edge of the inner covering is sutured to the lower edge of the outer covering to form the lower edge of the covering material, thus the support frame is enclosed in a space formed between the inner covering, the outer covering as well as the upper and lower edges of the covering material.

In an embodiment, the upper portion of the inner covering has three notches that matches the shape of the plurality of valve leaflets, and the lower portion of the inner covering matches the shape of the valve ring of the support frame. Between every two notches is a protrusion that matches the shape of the valve ridge of the support frame. Further, two protrusions are provided on two sides of the inner covering material respectively. These two protrusions will form a shape matching with a valve ridge of the support frame when combined.

In an embodiment, the upper portion of the outer covering has three protrusions matching the shape of the valve ridge of the support frame, and the lower portion of the outer covering matches the shape of the valve ring of the support frame. Between every two protrusions is a notch that match the shape of the valve leaflets. Further, two notches are provided on two sides of the outer covering respectively. These two notches, will form a shape matching with a valve leaflet when combined.

In an embodiment, the inner covering, the outer covering and the suture ring are formed as a single component.

In an embodiment, the outer covering and the suture ring are formed as a single component.

Preferably, each of the valve leaflets, the suture ring and the covering material are preset with suturing marks such that the heart valve bioprosthesis can be completely prepared by suturing along these suturing marks.

In an embodiment, the support frame is formed as a single component.

In an embodiment, the support frame is made of an elastic material.

In an embodiment, the distance between two adjacent suturing marks is 0.5-3 mm.

In an embodiment, the support frame is made of polyformaldehyde (POM), polyetheretherketone (PEET), polysulfone (PSF), Co-based alloy, Ti-based alloy, or Ni—Ti alloy.

In an embodiment, the valve auxiliary structure is made of animal pericardium, and the valve leaflets are made of animal pericardium or porcine aortic valve leaflets.

Preferably, the above animal pericardium is bovine, equine, porcine, ovine, caprine, or asinine pericardium.

The suturing marks may be a suturing hole, a suturing point, or other marks that are easy to identify.

Preferably, the suturing marks are preset at any position necessary for suturing during manufacturing of the heart valve bioprosthesis.

Preferably, the suturing marks are preset along the periphery of the inner covering, the periphery of the outer covering as well as the periphery of the suture ring.

According to another aspect of the present invention, a heart valve bioprosthesis is provided. The heart valve bioprosthesis comprises: a support frame, a plurality of valve leaflets and a valve auxiliary structure. The plurality of valve leaflets is connected to the valve auxiliary structure, the valve auxiliary structure is connected to the support frame, wherein the valve auxiliary structure is preset with suturing marks such that the heart valve bioprosthesis can be completely prepared by suturing along the suturing marks.

In an embodiment, the support frame is formed as a single component.

In an embodiment, the support frame is made of an elastic material.

In an embodiment, the valve auxiliary structure comprises a suture ring and a covering material, the plurality of valve leaflets is connected to the covering material, and the covering material and the suture ring are fixed directly or indirectly on the support frame.

In an embodiment, the covering material comprise an inner covering and an outer covering, wherein the plurality of valve leaflets is connected to the inner covering, and the support frame is placed within a space formed between the inner covering and the outer covering.

Preferably, the plurality of valve leaflets, the suture ring and the covering material are preset with suturing marks such that the heart valve bioprosthesis is completely prepared by suturing along the suturing marks.

In an embodiment, the plurality of valve leaflets and the valve auxiliary structure is made of biological tissues.

In an embodiment, the elastic material is polyformaldehyde (POM), polyetheretherketone (PEET), polysulfone (PSF), Co-based alloy, Ti-based alloy, or Ni—Ti alloy.

The suturing marks may be a suturing hole, a suturing point, or other marks that are easy to identify.

According to a further aspect of the present invention, a method for manufacturing a heart valve bioprosthesis is provided. The manufacturing method comprises the following steps:

a) providing a support frame, a plurality of valve leaflets, a suture ring and a covering material;

b) presetting suturing marks on the plurality of valve leaflets, the suture ring and the covering material;

c) suturing the plurality of valve leaflets to the covering material along the suturing marks, and fixing the sutured plurality of valve leaflets and covering material to the support frame;

d) fixing the suture ring to the support frame to form the heart valve bioprosthesis.

In an embodiment, the covering material comprises an inner covering and an outer covering, and step c) comprises: suturing the plurality of valve leaflets to the inner covering and suturing the outer covering to the inner covering to form upper and lower edges of the covering material.

Preferably, step c) comprises: placing the support frame into a space formed between the inner covering and the outer covering.

Preferably, step c) comprises: suturing the plurality of valve leaflets to the top edge of the inner covering and suturing the top edge of the outer covering to the top edge of the inner covering to form the upper edge of the covering material; and step c) comprises: suturing the lower edge of the inner covering to the lower edge of the outer covering to form the lower edge of the covering material, thus enclosing the support frame into a space surrounded by the inner side covering, the outer side covering as well as the upper and lower edges of the covering material.

Preferably, the support frame comprises a valve ring and a valve ridge which are formed as a single component; and step d) comprises: suturing the suture ring to an outer edge of the valve ring.

Preferably, the plurality of valve leaflets is sutured to the covering material by back stitching, and/or the upper edges of the inner and outer coverings are sutured together by blanket stitching.

In the above method, the suturing mark is a suturing hole, a suturing point, or other marks that are easy to identify.

The heart valve bioprosthesis of the present invention decreases the possibility of thrombus or bacterial attachment, is made by simple processing, has an excellent compliance with the cardiac tissue, and has a prolonged valve service life.

DETAILED DESCRIPTION OF THE INVENTION

Figure 1:
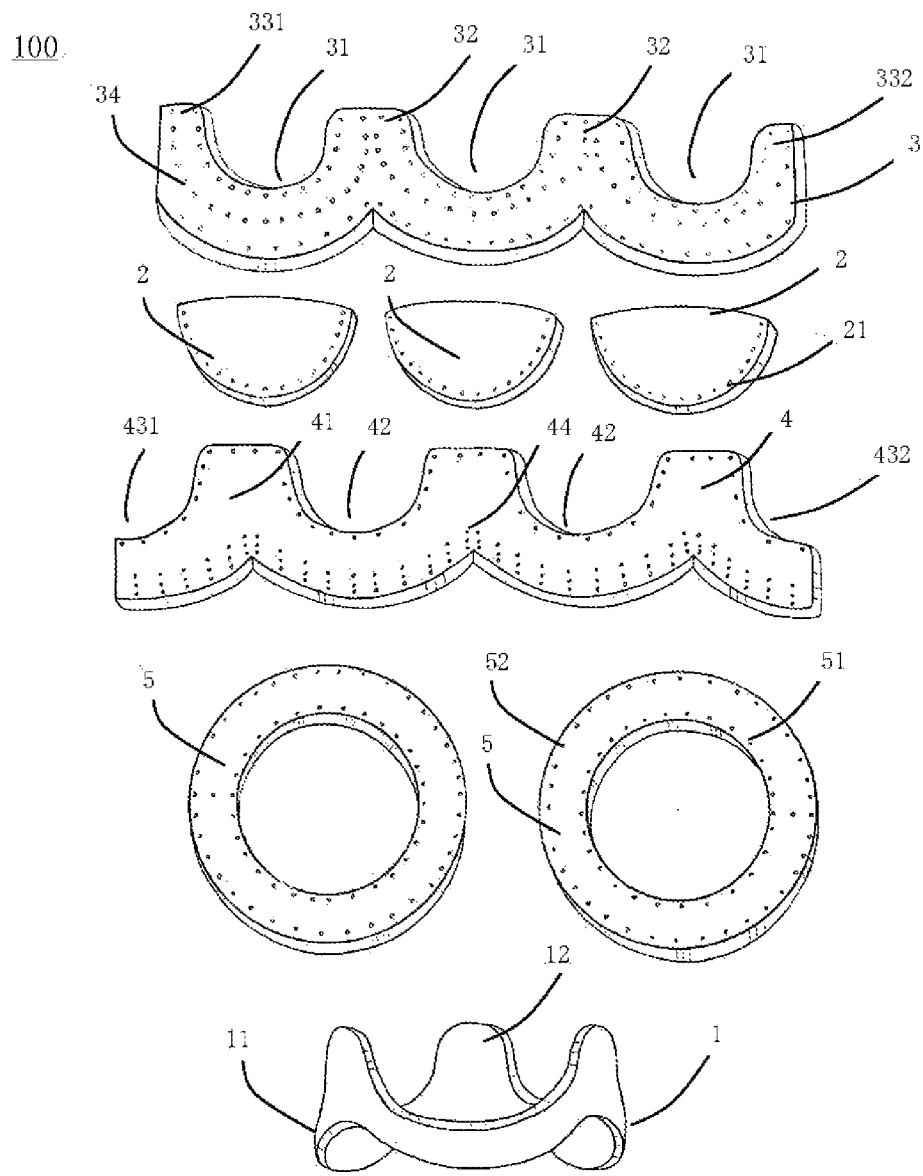
FIGS. 1A to 1E show the components of a heart valve bioprosthesis according to an embodiment of the present invention.
Figure 1A:
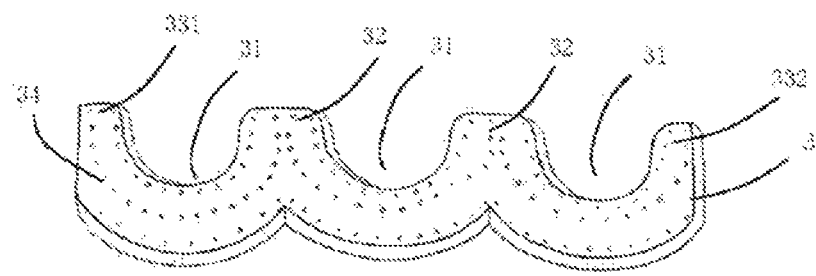
Figure 1B:
Figure 1C:
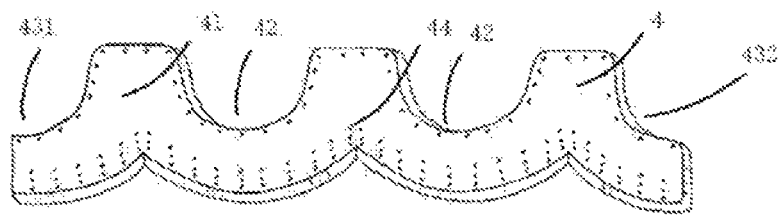
Figure 1D:
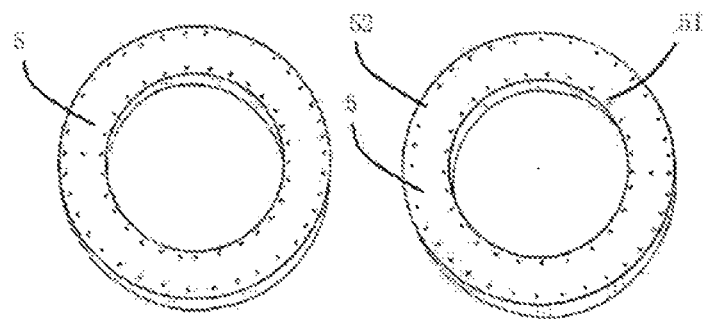
Figure 1E:
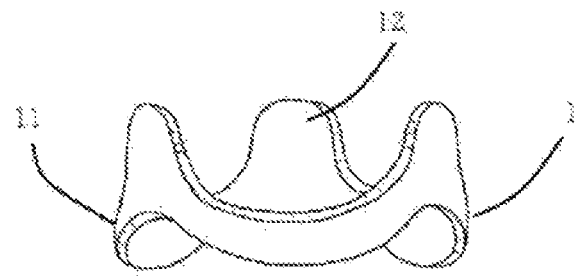

The preferred embodiments of the present invention will be explained in details with reference to the accompanying drawings, to make the objective(s), characteristics and advantages of the present invention better understood. It should be understood that the embodiments shown in the figures are not to limit the scope of the present invention; instead, they are provided only to explain the substantial spirit of the technical solutions of the present invention.

Definitions of Technical Terms

Support frame: an irregular circular ring comprising a valve ring (wave-like or flat) and a valve ridge (three ridged bulges); in a traditional heart valve bioprosthesis, the support frame is formed by combining valve wires and a valve base, wherein the valve wires are in the shape of an irregular circular ring and is formed by the valve ridge (three bulged ridges), while the valve base is circular, either flat or in wave-like shape. In the heart valve bioprosthesis of the present invention, the support frame is formed as a single component.

Valve leaflet: it is formed by suturing with an animal pericardium (bovine, equine, porcine, ovine, caprine, or asinine pericardium) and/or with porcine aortic valve leaflets.

Suture edge (or the so-called suture ring): the suture edge is used for fixing the heart valve prosthesis to the cardiac tissue; it is found on the outer edge of the support frame, and is generally formed in a ring shape (or it may be in other shape) by suturing, thus sometimes being called as the suture ring.

Covering material: material to be sutured to the inner and outer edges and upper and lower edges of the support frame.

Valve auxiliary structure: a general term encompassing the suture ring and covering material.

FIGS. 1A to 1E show the components of a heart valve bioprosthesis according to an embodiment of the present invention. As shown in FIGS. 1A to 1E, the heart valve bioprosthesis (100) comprises: a support frame (1), a plurality of valve leaflets (2), an inner covering (3), an outer covering (4), and a suture ring (5), wherein the plurality of valve leaflets (2) is sutured to the inner covering (3), the outer covering 4 is sutured to the inner covering (3), and then the plurality of valve leaflets (2), the inner covering (3) and the outer covering (4) are together mounted to the support frame (1) and sutured to the support frame (1), that is, the support frame is placed within a space formed between the inner covering (3) and the outer covering (4). Finally, the suture ring (5) is fixed onto the support frame, thus forming the complete heart valve bioprosthesis. Herein, the inner covering (3), the outer covering (4) and the suture ring (5) may be collectively called the valve auxiliary structure. The inner covering (3) and the outer covering (4) may be collectively called the covering material. Herein, the suture ring may be fixed to the support frame by suturing to the inner covering and/or the outer covering, or may be sutured directly to the support frame.

The support frame (1) comprises a valve ring (11) and a valve ridge (12) which are formed as one, wherein the valve ring (11) is in a shape of an irregular circular ring and the valve ridge (12) comprises three ridged bulges. Preferably, the support frame (1) is formed as a single component by an elastic material. Preferably, the support frame (1) does not have holes or slots. More preferably, the support frame is made of polyformaldehyde (POM), polyetheretherketone (PEET), polysulfone (PSF), Co-based alloy, Ti-based alloy, or Ni—Ti alloy.

The plurality of valve leaflets (2) is substantially semi-circular and preset with suturing holes (21) for suturing the plurality of valve leaflets (2) to the inner covering (3). A heart valve generally comprises three valve leaflets (2). The valve leaflets are made of biological tissues. Preferably, the valve auxiliary structure is made of animal pericardium, and the plurality of valve leaflets is made of animal pericardium or porcine aortic valve leaflet. The animal pericardium is bovine, equine, porcine, ovine, caprine, or asinine pericardium or pericardium from any suitable animal.

The inner covering (3) is provided at its upper portion with three notches (31) matching in shape with the plurality of valve leaflets (2), and has a lower portion with a profile matching in shape with the valve ring of the support frame. Between any two notches (31), a protrusion (32) is provided, matching in shape with the valve ridge of the valve frame. Further, on two sides of the inner covering (3), a protrusion (331) and a protrusion (332) are provided, respectively. The protrusions (331 and 332) will form a shape matching with the valve ridge of the valve frame when combined. The inner covering is preset with suturing holes (34) used for suturing it with the valve leaflets and the outer covering (4). In the present embodiment, the suturing holes are arranged along the periphery of the inner covering, and a row of suturing holes is further provided in the middle portion of the inner side covering. However, it should be understood that the suturing holes (34) may be preset on any site of the inner covering necessary for suturing during manufacturing of the heart valve bioprosthesis. The inner covering is made of biological tissues. Preferably, the biological tissue is an animal pericardium, such as bovine, equine, porcine, ovine, caprine, or asinine pericardium, or any suitable animal.

The outer covering (4) is provided at its upper portion with three protrusions (41) matching in shape with the valve ridge of the support frame, and has a lower portion with a profile matching in shape with the valve ring of the support frame. Between any two protrusions (41), a notch (42) is provided, matching in shape with the valve leaflet (2). Further, on two sides of the outer covering (4), a notch (431) and a notch (432) are provided, respectively. The notches (431 and 432), if combined, may form a shape matching with the shape of one valve leaflet (2). The outer covering is preset with suturing holes (44) for suturing it together with the inner covering (4). In the present embodiment, the suturing holes are arranged along the periphery of the outer covering, and a row of suturing holes is further provided in the middle portion of the inner covering. However, it should be understood that the suturing holes (44) may be preset on any site of the outer covering necessary for suturing during provided on or near the position to be sutured. The operator, when suturing the heart valve bioprosthesis, may perform suturing along these suturing marks. Preferably, a distance between two adjacent suturing marks is 0.5-3 mm, more preferably 1.4-2 mm. The manner of providing the suturing marks may comprise laser drilling, jig & fixture drilling (similar in principle to a paper hole puncher), etc. In addition, the suturing marks may be provided at any position necessary for suturing, on one or more of the valve leaflets (2), the inner covering (3), the outer covering (4) and the suture ring (5), without being limited to the position(s) disclosed herein.

In comparison with the heart valve bioprosthesis in the prior art, the heart valve bioprosthesis of the present invention uses the special support frame and biological tissues covering and presets the suturing marks, and thus improves the compliance with the heart and the biocompatibility with the human body, reduces the total height of the valve, shortens the suturing time, and decreases the possibility of thrombus or bacterial attachment, as detailed in the following Table 1.

TABLE 1 compares several examples of the heart valve bioprosthesis of the present invention with those in the prior art.

| | Examples | Valve type | Valve support frame | Covering material | Valve leaflet material | Suturing holes | Support frame formed as a single component | Total valve height (mm) | Suturing time (hour) | thrombus or bacterial attachment |
|---|---|---|---|---|---|---|---|---|---|---|
| The present invention | Example 1 | A21 aortic valve | POM | Bovine pericardium | Bovine pericardium | yes | yes | 12 | 2.5 | Level 3 |
| | Example 2 | A21 aortic valve | PEET | Equine pericardium | Bovine pericardium | yes | yes | 12 | 2.5 | Level 3 |
| | Example 3 | M25 mitral valve | Ni—Ti alloy | Porcine pericardium | Porcine aortic valve leaflet | yes | yes | 14.5 | 2.5 | Level 3 |
| Existing art | Comparison example 1 | A21 aortic valve | Stainless steel | terylene | Bovine pericardium | no | no | 14-15 | 4 | Level 1 |
| | Comparison example 2 | A21 aortic valve | plastic | terylene | Equine pericardium | no | yes | 14-15 | 4 | Level 1 |
| | Comparison example 3 | M25 mitral valve | plastic | terylene | Bovine pericardium | no | no | 15-18 | 4 | Level 1 |

Note:
the levels for thrombus or bacterial attachment are classified as below:
Level 1 refers to "high possibility of bacterial attachment or thrombus occurrence, with a proportion of 1.0% or less".
Level 2 refers to "low possibility of bacterial attachment or thrombus occurrence, with a proportion of 0.1% or less".
Level 3 refers to "very low possibility of bacterial attachment or thrombus occurrence, with a proportion of 0.01% or less".

manufacturing of the heart valve bioprosthesis. The outer covering (4) is made of biological tissues. Preferably, the biological tissue is an animal pericardium, such as bovine, equine, porcine, ovine, caprine, or asinine pericardium or any suitable animal.

The suture ring (5) is a circular ring, and is preset at its inner edge and outer edge with suturing holes (51 and 52), wherein the suturing holes (51) on the inner edge are used for suturing it to the outer covering while the suturing holes (52) on the outer edge are used for suturing two suture rings (5) together. The suture ring (5) is made of biological tissues. Preferably, the biological tissue is an animal pericardium, such as bovine, equine, porcine, ovine, caprine, or asinine pericardium, or any suitable animal.

It should be pointed out that the suturing holes provided on the valve leaflet (2), the inner covering (3), the outer covering (4) and the suture ring (5) may be substituted with other suturing marks, such as colored points or other marks FIGS. 2-10 show a method for manufacturing a heart valve bioprosthesis according to an embodiment of the present invention. The method of the present invention comprises the following steps:

e) providing a support frame, a plurality of valve leaflets, a covering material and a suture ring;
f) presetting suturing holes on the plurality of valve leaflets, the suture ring and the covering material;
g) suturing the plurality of valve leaflets to the covering material along the suturing holes;
h) fixing the sutured plurality of valve leaflets and covering material to the support frame;
i) fixing the suture ring to the support frame to form the heart valve bioprosthesis.

As shown in FIGS. 2-10, the support frame (1) in the present embodiment is formed as a single component, and there are three valve leaflets. The covering material consists of an inner covering (3) and an outer covering (4). There are two suture rings (5). It should be understood that the manufacturing method of the present invention is applicable to other similar heart valve bioprosthesis. The manufacturing method of the present invention follows a basic principle of presetting suturing holes on the valve leaflets, the covering material and the suture ring such that manufacturing of the heart valve simply requires suturing along the preset suturing holes, thus simplifying the manufacturing process and easy for product standardization.

Figure 2:
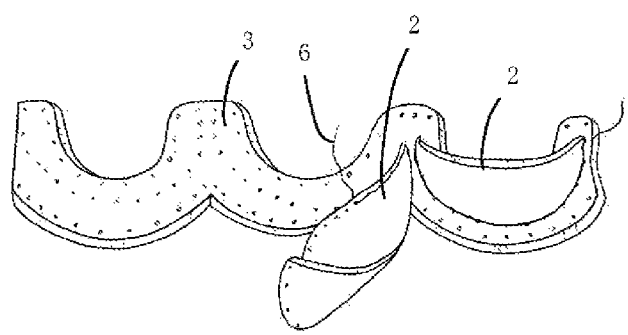
FIGS. 2-10 show a method for manufacturing of a heart valve bioprosthesis according to an embodiment of the present invention.
Figure 3:
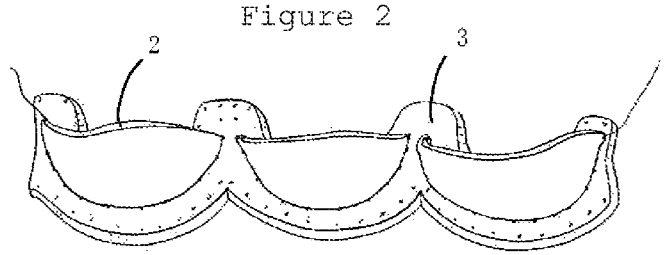
Figure 4:
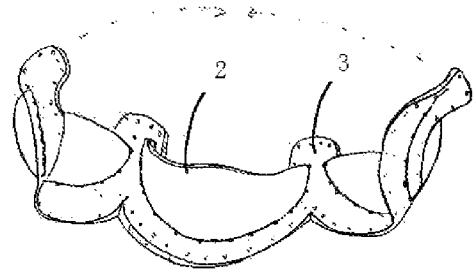
Figure 5:
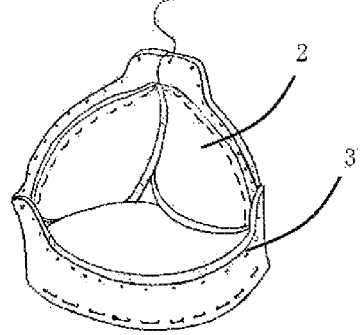

Specifically, the suture thread (6) first sutures the valve leaflets (2), one by one, onto the inner covering (3), along the suturing holes, that is, the valve leaflets are sutured to the top edge of the inner covering, as shown in FIGS. 2 and 3. During suturing, the valve leaflets are preferably sutured to the inner covering by back stitching. Next, the inner covering (3) is curled to form a cylinder-like shape and its two ends are sutured together, as shown in FIGS. 4-5.

Figure 6:
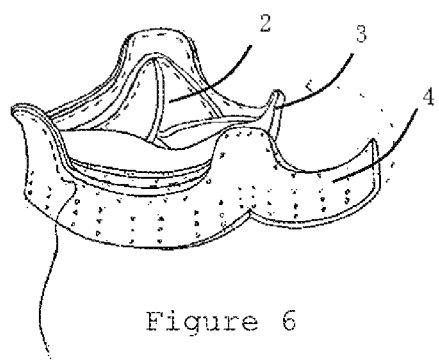

Then, the suture thread (6) sutures the outer covering (4) to the inner covering (3), along the suturing holes, that is, the top edge of the outer covering (4) is sutured to the top edge of the inner covering (3), as shown in FIG. 6. When suturing the outer covering (4) to the inner covering (3), the upper edges of the inner and outer coverings are preferably sutured together by blanket stitching.

Figure 7:
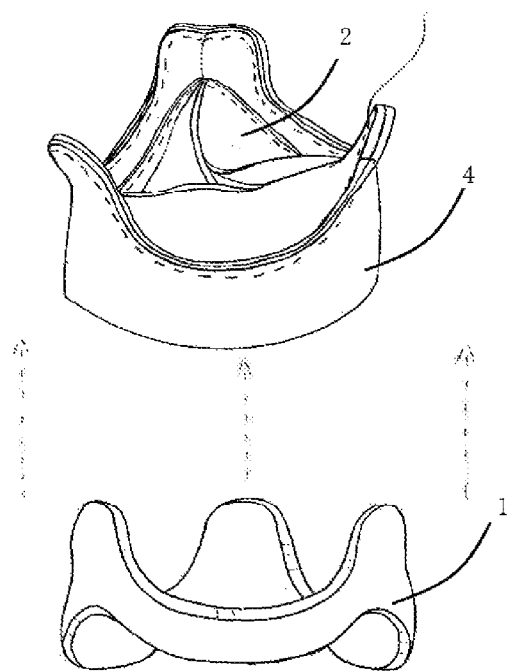
Figure 8:
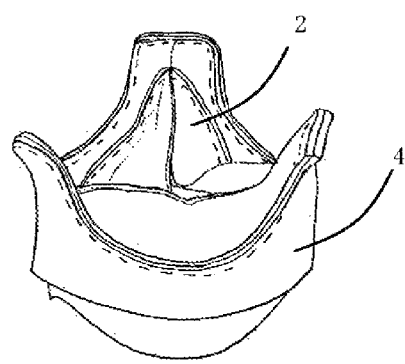
Figure 9:
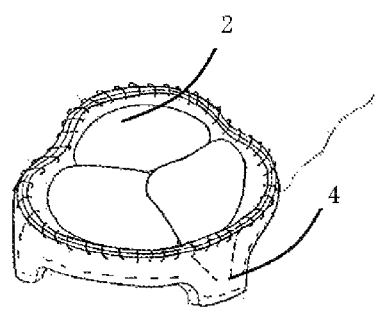
Figure 10:
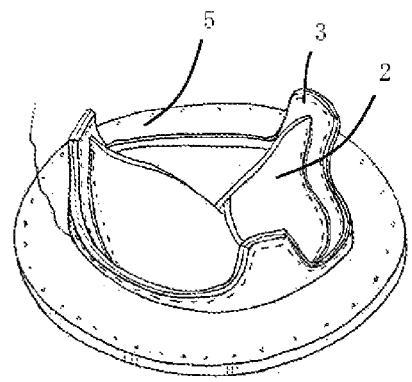

Next, the sutured valve leaflets (2), inner covering (3) and outer covering (4) are mounted onto the support frame (1) such that the support frame (1) is placed within a space formed between the inner covering (3) and the outer covering (4). Then, the lower edges of the inner and outer coverings are sutured together along the suturing holes, as shown in FIGS. 7-9. During such suturing, the lower edges of the inner and outer coverings are preferably sutured together by blanket stitching.

Finally, the suture thread (6) sutures the suture ring (5) to the outer side edge of the valve ring of the support frame along the suturing holes. Specifically, the inner edges of the two suture rings are sutured to the outer covering by couching stitch, and then the outer edges of the two suturing rings are sutured together by oversewing stitch. After suturing the suture ring, a certain outer edge is retained to facilitate suturing it into the heart or the aorta in a valve replacement operation.

Therefore, the manufacturing of the heart valve bioprosthesis of the present invention is completed.

It should be pointed out that the structure and shape of the heart valve bioprosthesis of the present invention are not limited to the above structure and shape. For example, the inner and outer coverings may be formed as a single component and separated into the inner and outer coverings after suturing to the support frame.

Figure 11:
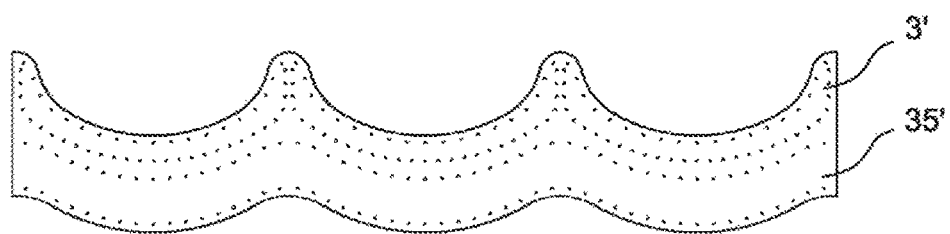
FIGS. 11 and 12 show the structures of the inner and outer coverings, respectively, of a heart valve bioprosthesis according to a second embodiment of the present invention.
Figure 12:
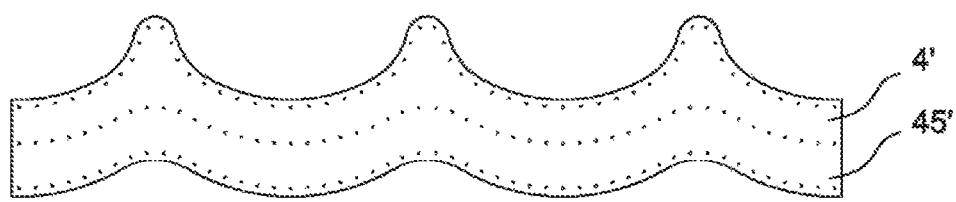

FIGS. 11 and 12 show structure of the inner covering (3') and the outer covering (4'), respectively, of a heart valve bioprosthesis according to a second embodiment of the present invention. The present embodiment differs from that shown in FIGS. 1A to 1E in that the suture ring is part of the inner and outer coverings. Specifically, the lower edges (35') and (45') of the inner and outer coverings are extended such that after suturing, the lower edges (35') and (45') of the inner and outer coverings (3') and (4') form the suture ring. Accordingly, the suture ring is not provided separately in the present embodiment unlike that shown in FIGS. 1A to 1E. In the present embodiment, the structures of the upper portions of the inner and outer coverings (3') and (4') and the structure of the support frame are same as the embodiment of FIGS. 1A to 1E, and thus will not be described in detail.

Figure 13:
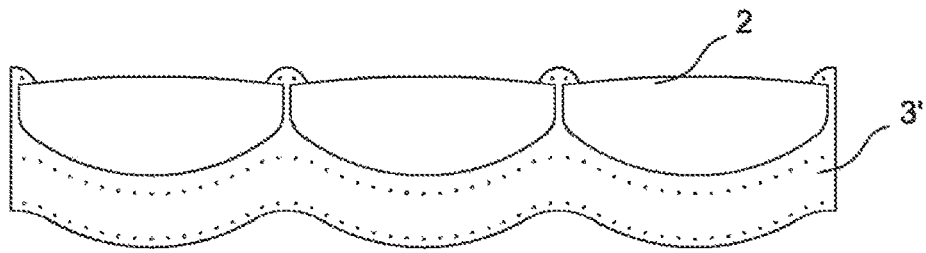
FIGS. 13-17 show the manufacturing steps of the heart valve bioprosthesis in FIGS. 11 and 12.

In the present embodiment, as shown in FIGS. 13-17, the suturing steps are set forth as below:

1) suturing the plurality of valve leaflets (2) to the inner covering (3') by back stitching, as shown in FIG. 13.

Figure 14:
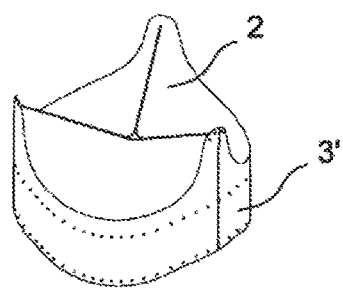

2) curling the inner covering (3') to form a cylinder-like shape and suturing its two ends together, as shown in FIG. 14.

Figure 15:
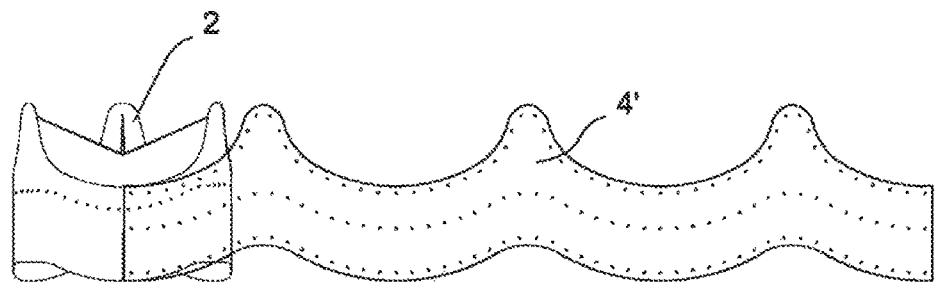

3) suturing the upper edges of the inner and outer coverings (3') and (4') together by blanket stitching, as shown in FIG. 15.

Figure 16:
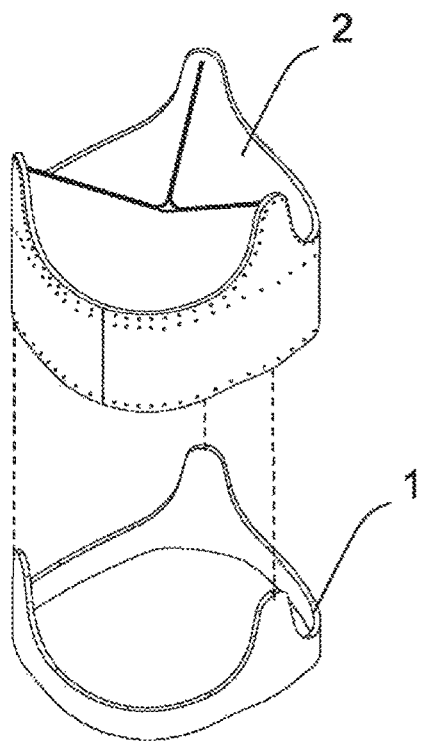

4) placing the support frame (1) between the inner and outer coverings, as shown in FIG. 16.

Figure 17:
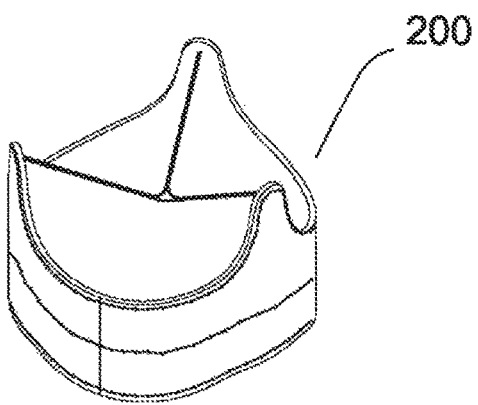

5) suturing the lower edges of the inner and outer coverings (3') and (4') together by a blanket stitching, to form the heart valve bioprosthesis (200), as shown in FIG. 17.

Figure 18:
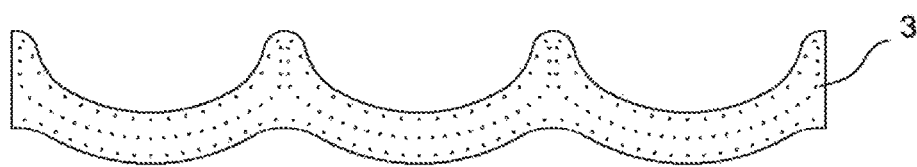
FIGS. 18 and 19 show the structures of the inner and outer coverings, respectively, of a heart valve bioprosthesis according to a third embodiment of the present invention.
Figure 19:
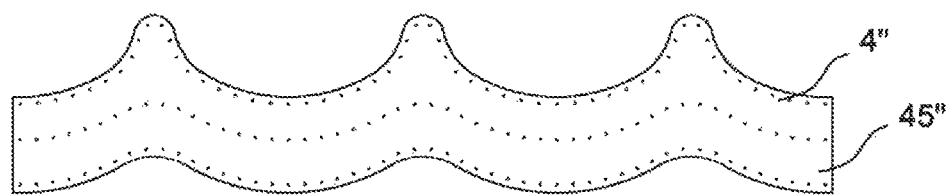

FIGS. 18 and 19 show the structure of the inner covering (3) and the outer covering (4"), respectively, of a heart valve bioprosthesis according to a third embodiment of the present invention. The present embodiment differs from that shown in FIGS. 1A to 1E in that the suture ring is formed as part of the outer covering (4"). Specifically, the lower edge (45") of the outer covering (4") is extended such that after suturing, the lower edge (45") of the outer covering (4") forms the suture ring. Accordingly, the suture ring is not provided separately in the present embodiment unlike FIGS. 1A to 1E. In the present embodiment, the structure of the inner covering (3) is same as that of the inner covering (3) in FIGS. 1A to 1E, and the structure of the upper portion of the outer covering (4") and the structure of the support frame (1) are same as those of the embodiment of FIGS. 1A to 1E, and thus will not be described in detail.

Figure 20:
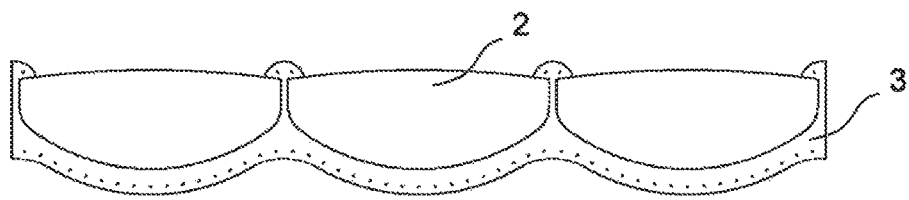
FIGS. 20-24 show the manufacturing steps of the heart valve bioprosthesis in FIGS. 18 and 19.

In the present embodiment, as shown in FIGS. 20-24, the suturing steps are set forth as below:

6) suturing the plurality of valve leaflets (2) to the inner covering (3) by back stitching, as shown in FIG. 20.

Figure 21:
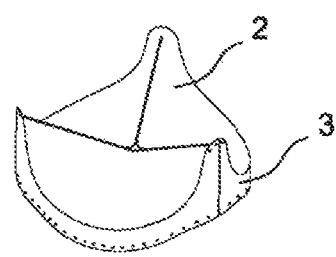

7) curling the inner covering (3) to form a cylinder-like shape and suturing its two ends together, as shown in FIG. 21.

Figure 22:
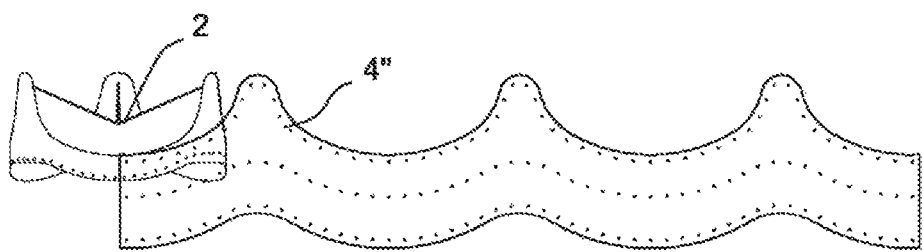

8) suturing the upper edges of the inner and outer side coverings (3) and (4") together by blanket stitching, as shown in FIG. 22.

Figure 23:
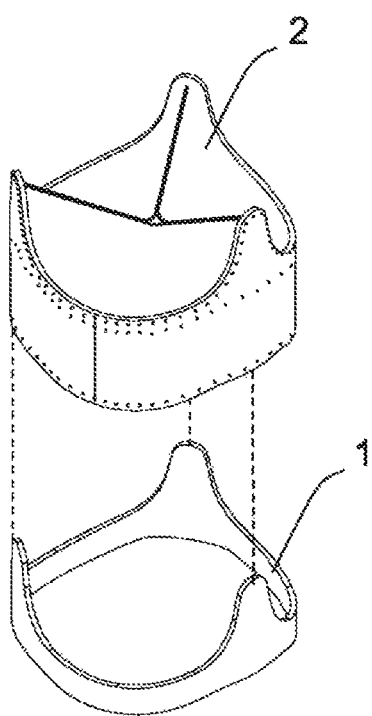

9) placing the support frame (1) between the inner and outer coverings, as shown in FIG. 23.

Figure 24:
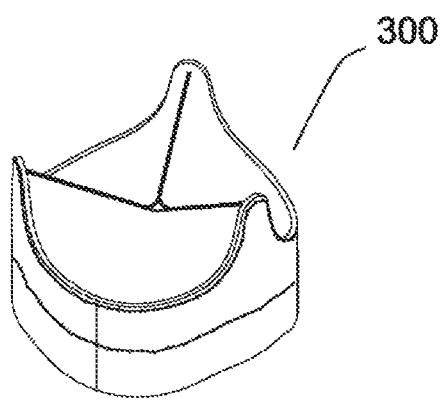

10) suturing the lower edges of the inner and outer coverings (3) and (4") together by blanket stitching, to form the heart valve bioprosthesis (300), as shown in FIG. 24.

Figure 25:
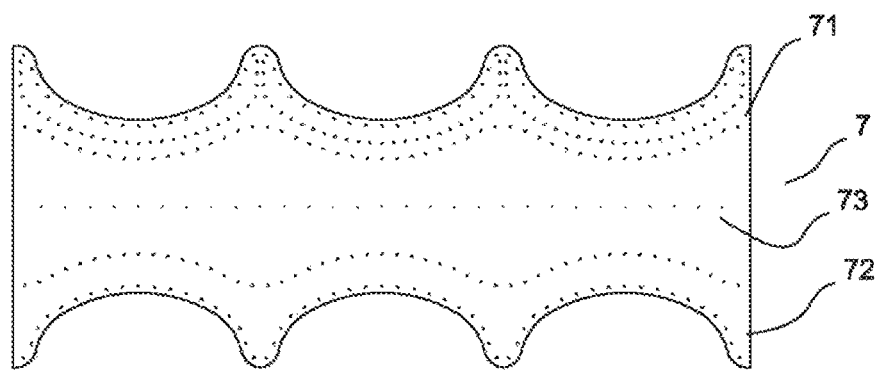
FIG. 25 shows the structure of the covering material of a heart valve bioprosthesis according to a fourth embodiment of the present invention.

FIG. 25 shows the structure of covering material (7) of a heart valve bioprosthesis according to a fourth embodiment of the present invention. The present embodiment differs from that shown in FIGS. 1A to 1E in that the inner covering, the outer covering and the suture ring are formed as a single component. Specifically, in the present embodiment, the upper portion (71) of the covering material (7) is the inner covering, and its structure is same as the inner covering shown in FIGS. 1A to 1E and thus will not be described in detail herein. The lower portion (72) of the covering material (7) is the outer covering, and its structure is same as the outer covering shown in FIGS. 1A to 1E and thus will not be described in detail herein. The middle portion (73) of the covering material (7), after suturing, forms the suture ring. In the present embodiment, the support frame has the same structure as that of the support frame in FIGS. 1A to 1E and thus will not be described in detail herein.

Figure 26:
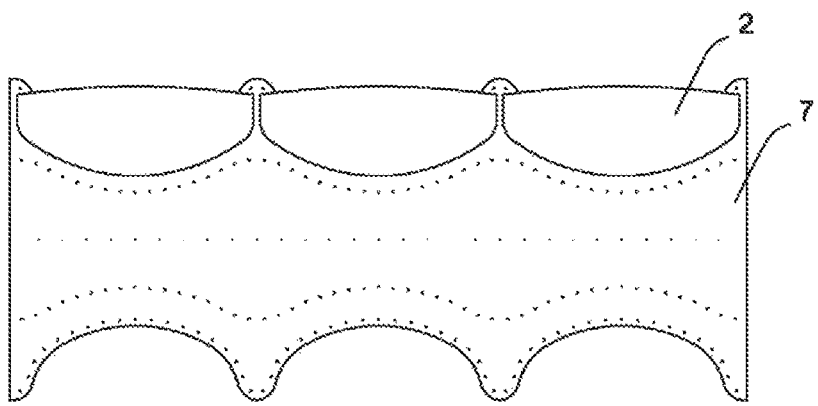
FIGS. 26-30 show the manufacturing steps of the heart valve bioprosthesis in FIG. 25.

In the present embodiment, as shown in FIGS. 26-30, the suturing steps are set forth as below:

11) suturing the plurality of valve leaflets (2) to the upper portion (71) (i.e. the inner side covering) of the covering material (7) by blanket stitching, as shown in FIG. 26.

Figure 27:
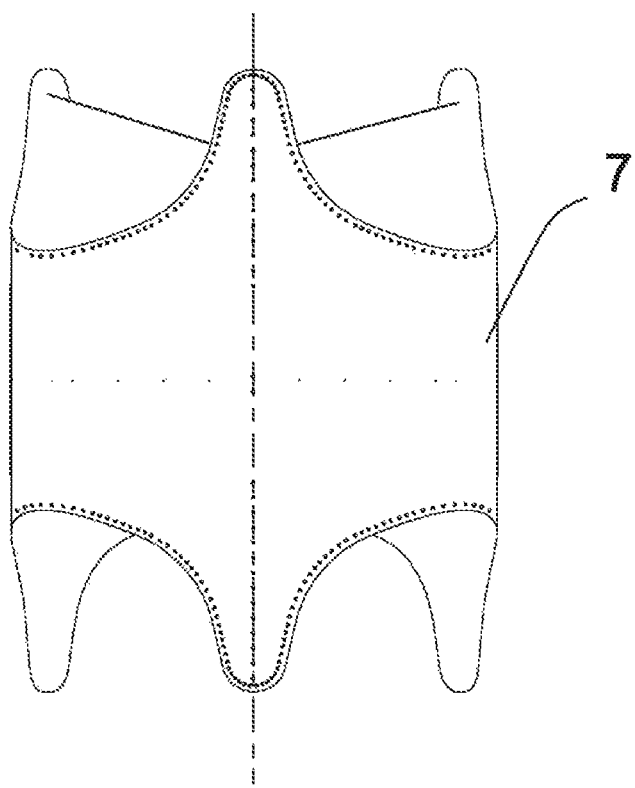

12) curling the covering material (7) to form a cylinder-like shape and suturing its two ends together, as shown in FIG. 27.

Figure 28:
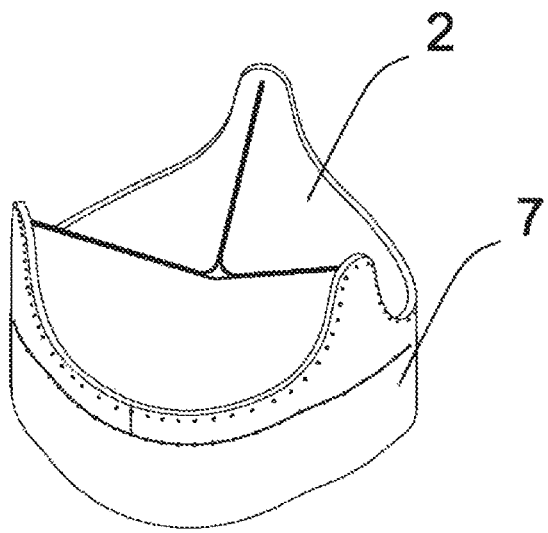

13) folding the lower portion (72) (i.e. the outer covering) of the covering material (7) upward to overlap and align with the upper portion (71) (i.e. the inner covering) of the covering material (7), thus forming the inner and outer coverings, as shown in FIG. 28.

Figure 29:
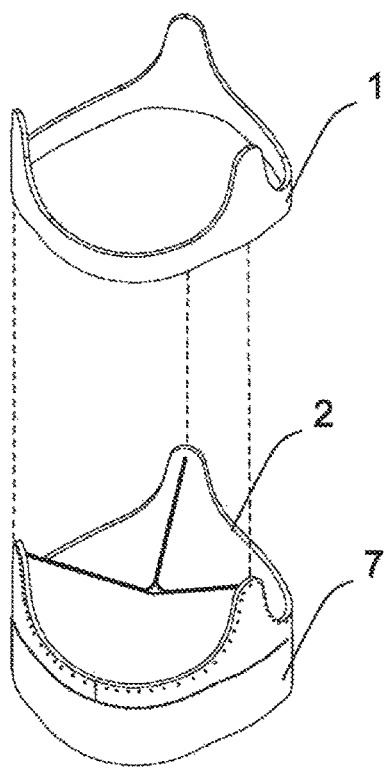

14) placing the support frame (1) between the inner and outer coverings, as shown in FIG. 29.

Figure 30:
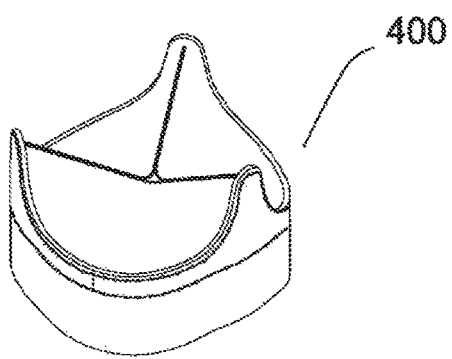

15) suturing the upper edges of the inner and outer coverings together by blanket stitching to form the heart valve bioprosthesis (400), as shown in FIG. 30.

In the above, the valve auxiliary structure is made of biological tissues but, also included in the scope of this invention are those valve auxiliary structures (such as the covering material and the suture ring) having other materials internally and covered at its outer face with a layer of biological tissues, and other variations.

In the heart valve bioprosthesis of the present invention, in addition to the valve leaflets being made of biological tissues, the valve auxiliary structure (the covering material, the suture ring, etc.) is also substantially made of biological tissues. Since the terylene fabric used in the prior traditional heart valve bioprosthesis for the covering material and suture ring is not considered by this invention, the heart valve auxiliary structure of the present invention is made purely of biological tissues. The applicant overcome problems with the terylene fabric for the covering material and suture ring (as mentioned in the background, the terylene fabric has many advantages, and thus with the teaching from the prior art, those skilled in the art generally use only the terylene fabric to make the covering material and suture ring in the stented heart valve bioprosthesis) by using only biological tissues to directly contact the blood, thus decreases the possibility of thrombus or bacterial attachment.

In the heart valve bioprosthesis of the present invention, the support frame is formed as a single component using high elastic and high toughness material. This results in a heart valve bioprosthesis that has the advantages of traditional stented valves (support frame) such as precise positioning and easy implantation, but also has the advantages of traditional stentless valves (no support frame) such as excellent compliance. Also, the heart valve bioprosthesis of this invention eliminates the disadvantages of traditional stented valves (support frame) such as high strength, high hardness, complicated and risky support frame structure, and also eliminates the disadvantages of traditional stentless valves (no support frame) such as difficult positioning during implantation. The heart valve of this invention is made by simple processing, exhibit excellent compliance with the cardiac tissue, and has a prolonged valve service life. It can be precisely positioned during an implantation operation, and is easy for the surgeons to use and handle. Also, the valve designed according to the present invention is decreased in height by about 15-18% compared with the prior heart valve bioprosthesis available in the market, thus lowering the risk of a relatively large height of the prior heart valve bioprosthesis.

In addition, in the present invention, the valve leaflets, suture ring and covering material are sutured in a new cutting state and suturing method(s) such that the valve suturing process is standardized. Specifically, the sites for suturing are preset with holes, thus first establishing standardization of needle spacing during suturing such that the suturing process is more concise, precise and standardized. Four stitching methods, i.e. back stitching, blanket stitching, running stitching, and oversewing stitching, are used, thus ensuring the sutures are firmly secured and the heart valve bioprosthesis exhibits better and more reliable performance in comparison to similar products.

The preferred embodiments of the present invention are described in detail as above. However, it should be understood that upon reading the above teachings of the present invention, those skilled in the art can make changes or modifications to the present invention. These equivalent solutions will also fall within the protection scope defined by the claims as attached in the present application.

What is claimed is:

1. A heart valve bioprosthesis comprising a support frame, valve leaflets and a valve auxiliary structure, said valve leaflets are connected to the valve auxiliary structure, and said valve auxiliary structure is connected to the support frame; wherein
    said valve leaflets are made from animal pericardium or porcine aortic valve leaflets;
    said valve auxiliary structure is made from animal pericardium and comprises a suture ring and a covering material, said covering material comprising an inner covering and an outer covering; wherein said support frame is placed within a space formed between the inner covering and the outer covering;
    said valve leaflets, said suture ring and said covering material are preset with suturing marks so that the distance between two adjacent suturing marks is 0.5-3 mm; wherein suturing along the suturing marks produces said heart valve bioprosthesis;
    said support frame is made of an elastic material; and
    said suture ring is for suturing to cardiac tissues.

2. The heart valve bioprosthesis of claim 1, wherein the valve leaflets are connected to the covering material, and the covering material and the suture ring are fixed directly or indirectly on the support frame.

3. The heart valve bioprosthesis of claim 2, wherein the valve leaflets are connected to the inner covering.

4. The heart valve bioprosthesis of claim 1, wherein the suturing marks are suturing holes.

5. The heart valve bioprosthesis of claim 1, wherein the support frame is formed as a single component.

6. The heart valve bioprosthesis of claim 1, wherein the support frame is made of polyformaldehyde (POM), polyetheretherketone (PEEK), polysulfone (PSF), Co-based alloy, Ti-based alloy, or Ni—Ti alloy.

7. The heart valve bioprosthesis of claim 1, wherein the animal pericardium is bovine, equine, porcine, ovine, caprine, or asinine pericardium.

8. A method of manufacturing the heart valve bioprosthesis of claim 1, comprising the following steps:
    a) providing a support frame, valve leaflets, a suture ring and a covering material;
    b) presetting suturing marks on the valve leaflets, the suture ring and the covering material;
    c) suturing the valve leaflets to the covering material along the suturing marks, and fixing the sutured valve leaflets and covering material to the support frame; and
    d) fixing the suture ring to the support frame to form said heart valve bioprosthesis.

9. The method of claim 8, wherein step c) comprises suturing the valve leaflets to the inner covering and then suturing the outer covering to the inner covering to form upper and lower edges of the covering material.

10. The method of claim 9, wherein step c) further comprises placing the support frame into a space formed between the inner covering and the outer covering.

11. The method of claim 9, wherein step c) comprises suturing the valve leaflets to a top edge of the inner covering and suturing a top edge of the outer side covering to the top edge of the inner side covering to form said upper edge of the covering material; and suturing a lower edge of the inner side covering to a lower edge of the outer covering to form said lower edge of the covering material; wherein the support frame is enclosed in a space formed between the inner covering, the outer covering and the upper and lower edges of the covering material.

12. The method of claim 8, wherein when the support frame comprises a valve ring and a valve ridge which are formed as a single component; step d) comprises suturing the suture ring to an outer edge of said valve ring.

13. The method of claim 8, wherein the suturing marks are suturing holes.

* * * * *